US008968707B2

(12) United States Patent
Gringore et al.

(10) Patent No.: US 8,968,707 B2
(45) Date of Patent: Mar. 3, 2015

(54) COMPOSITION PACKAGED IN AN AEROSOL DEVICE, COMPRISING AT LEAST ONE ANIONIC FIXING POLYMER, AT LEAST ONE SILICONE OXYALKYLENATED IN THE ALPHA AND OMEGA POSITIONS OF THE SILICONE CHAIN, AND AT LEAST ONE PROPELLANT

(75) Inventors: Charles Gringore, Paris (FR); Françoise Pataut, Paris (FR)

(73) Assignee: L'Oreal, Paris (FR)

( * ) Notice: Subject to any disclaimer, the term of this patent is extended or adjusted under 35 U.S.C. 154(b) by 951 days.

(21) Appl. No.: 11/124,229

(22) Filed: May 9, 2005

(65) Prior Publication Data

US 2005/0265929 A1 Dec. 1, 2005

Related U.S. Application Data

(60) Provisional application No. 60/620,337, filed on Oct. 21, 2004.

(30) Foreign Application Priority Data

May 7, 2004 (FR) .................................... 04 04991

(51) Int. Cl.
| A61K 8/00 | (2006.01) |
| A61K 9/00 | (2006.01) |
| A61Q 5/06 | (2006.01) |
| A61K 8/04 | (2006.01) |
| A61K 8/81 | (2006.01) |
| A61K 8/894 | (2006.01) |

(52) U.S. Cl.
CPC . *A61Q 5/06* (2013.01); *A61K 8/046* (2013.01); *A61K 8/8147* (2013.01); *A61K 8/894* (2013.01); *A61K 2800/5424* (2013.01)
USPC .......................................................... 424/49

(58) Field of Classification Search
None
See application file for complete search history.

(56) References Cited

U.S. PATENT DOCUMENTS

| 2,047,398 | A | 7/1936 | Voss et al. |
| 2,723,248 | A | 11/1955 | Wright |
| 3,579,629 | A | 5/1971 | Viout et al. |
| 3,716,633 | A | 2/1973 | Viout et al. |
| 3,810,977 | A | 5/1974 | Levine et al. |
| 3,925,542 | A | 12/1975 | Viout et al. |
| 3,946,749 | A | 3/1976 | Papantoniou |
| 3,966,403 | A | 6/1976 | Papantoniou et al. |
| 3,966,404 | A | 6/1976 | Papantoniou et al. |
| 4,128,631 | A | 12/1978 | Lundmark et al. |
| 4,129,711 | A | 12/1978 | Viout et al. |
| 4,137,208 | A | 1/1979 | Elliott |
| 4,282,203 | A | 8/1981 | Jacquet et al. |
| 4,289,752 | A | 9/1981 | Mahieu et al. |
| 4,871,529 | A | 10/1989 | Sramek |
| 5,804,166 | A * | 9/1998 | Chan et al. ...................... 424/47 |
| 5,972,356 | A | 10/1999 | Peffly et al. |
| 6,039,933 | A * | 3/2000 | Samain et al. .................. 424/47 |
| 6,319,489 | B1 | 11/2001 | Ashton et al. |
| 6,350,433 | B1 | 2/2002 | Ashton et al. |
| 6,426,079 | B1 * | 7/2002 | Bara et al. ...................... 424/401 |
| 6,541,017 | B1 | 4/2003 | Lemann et al. |
| 6,569,413 | B1 * | 5/2003 | Hessefort et al. ........... 424/70.11 |
| 2004/0170588 | A1 | 9/2004 | Bara et al. |

FOREIGN PATENT DOCUMENTS

| DE | 2 330 956 | 1/1974 |
| EP | 0 945 130 A2 | 9/1999 |
| EP | 0 968 708 A1 | 1/2000 |
| EP | 1 019 013 | 7/2000 |
| FR | 1 222 944 | 6/1960 |
| FR | 1 564 110 | 4/1969 |
| FR | 1 580 545 | 9/1969 |
| FR | 2 265 781 | 10/1975 |
| FR | 2 265 782 | 10/1975 |
| FR | 2 350 384 | 12/1977 |
| FR | 2 357 241 | 2/1978 |
| FR | 2 439 798 | 5/1980 |
| FR | 2 751 221 | 1/1998 |
| GB | 839 805 | 6/1960 |
| GB | 922 457 | 4/1963 |
| GB | 1 572 626 | 7/1980 |
| LU | 75 370 | 7/1976 |
| LU | 75 371 | 7/1976 |
| WO | WO 00/69398 | 11/2000 |

OTHER PUBLICATIONS

English language Derwent Abstract of FR 2 357 241, Mar. 2, 1978.
French Search Report for FR 04 04991 (French Priority Application for U.S. Appl. No. 11/124,229, the present application) dated Feb. 7, 2005.

* cited by examiner

*Primary Examiner* — Trevor Love
(74) *Attorney, Agent, or Firm* — The Marbury Law Group, PLLC

(57) ABSTRACT

The present disclosure is directed to a composition packaged in an aerosol device comprising at least one anionic fixing polymer, at least one α and ω oxyalkylenated silicone and at least one propellant, and also to a cosmetic hair treatment process using such compositions and to a process of styling the hair using such a composition.

18 Claims, No Drawings

COMPOSITION PACKAGED IN AN AEROSOL DEVICE, COMPRISING AT LEAST ONE ANIONIC FIXING POLYMER, AT LEAST ONE SILICONE OXYALKYLENATED IN THE ALPHA AND OMEGA POSITIONS OF THE SILICONE CHAIN, AND AT LEAST ONE PROPELLANT

This application claims benefit of U.S. Provisional Application No. 60/620,337, filed Oct. 21, 2004, the contents of which are incorporated herein by reference. This application also claims benefit of priority under 35 U.S.C. §119 to French Patent Application No. 04 04991, filed May 7, 2004, the contents of which are also incorporated by reference.

The present disclosure relates to a composition packaged in an aerosol device and comprising at least one anionic fixing polymer, at least one α and ω oxyalkylenated silicone and at least one propellant, and also to a cosmetic hair treatment process using such compositions and to a process of styling the hair using such a composition.

It is known to use aerosol sprays in the field of hairstyling. These are formulations packaged in aerosol devices, which, on exiting the aerosol device, are in the form of fine droplets after spraying and thus form a spray.

These formulations generally comprise a fixing polymer and are used to structure the hairstyle and give it long-lasting hold.

However, certain fixing polymers may result in a hardening of the hair as a whole. This may lead to a set hairstyle and to disentangling that is often difficult at the end of the day, also possibly leaving the hair with a dry feel.

The present inventors have found, surprisingly, that the combination of at least one anionic fixing polymer, at least one silicone as described below and at least one propellant makes it possible to avoid at least one of the above-mentioned disadvantages.

Specifically, the composition according to the present disclosure may make it possible to obtain a smoother surface of the head of hair, and the hairs are held in the desired shape without being set or hardened.

In addition, the disentangling at the end of the day may be facilitated and the hair may remain supple and smooth.

Thus, the present disclosure relates to a composition packaged in an aerosol device comprising, in a cosmetically acceptable medium, at least one anionic fixing polymer, at least one silicone oxyalkylenated in the α and ω positions of the silicone chain, and at least one propellant.

Another embodiment disclosed herein relates to a cosmetic hair treatment process using the composition according to the disclosure.

In yet another embodiment, the present disclosure relates to a process for styling hair comprising applying to the hair with an aerosol device a composition as disclosed herein as a styling product.

Other subjects, characteristics, aspects and advantages of the disclosure will emerge even more clearly on reading the description and the concrete, but non-limiting, examples that follow.

According to the present disclosure, the above-described composition is packaged in an aerosol device and comprises, in a cosmetically acceptable medium, at least one anionic fixing polymer, at least one silicone oxyalkylenated in the α and ω positions of the silicone chain, and at least one propellant.

As used herein, the term "cosmetically acceptable medium" means a medium that is compatible with the hair.

As used herein, the term "fixing polymer" means any polymer capable of giving a head of hair a shape or of holding a given shape.

Anionic fixing polymers useful in the presently disclosed composition may be chosen from polymers comprising groups derived from carboxylic, sulfonic and/or phosphoric acids and that have a number-average molecular mass ranging from 500 to 50 000 000.

The carboxylic groups are chosen from unsaturated monocarboxylic and dicarboxylic acid monomers such as those of formula (I):

wherein:

n is a number ranging from 0 to 10;

$A_1$ is chosen from a methylene group, optionally connected to the carbon atom of the unsaturated group, or to the neighboring methylene group when n is greater than 1, via a hetero atom chosen from, for example, oxygen and sulfur;

$R_1$ is chosen from a hydrogen atom and phenyl and benzyl groups;

$R_2$ is chosen from a hydrogen atom, a lower $C_{1-4}$ alkyl group, for example a methyl or ethyl group, and a carboxyl group;

$R_3$ is chosen from a hydrogen atom, a lower alkyl group, a —$CH_2$—COOH group, a phenyl group, and a benzyl group.

The at least one anionic fixing polymer comprising carboxylic groups may be chosen, in at least one embodiment, from:

A) acrylic and methacrylic acid homo- and copolymers and salts thereof, for example, the products sold under the names Versicol® E or K by the company Allied Colloid and Ultrahold® by the company BASF; the copolymers of acrylic acid and of acrylamide sold in the form of their sodium salts under the names RETEN 421, 423 or 425 by the company Hercules; and the sodium salts of polyhydroxycarboxylic acids.

B) copolymers of acrylic and methacrylic acid with a monoethylenic monomer such as ethylene, styrene, vinyl esters, acrylic and methacrylic acid esters, optionally grafted onto a polyalkylene glycol such as polyethylene glycol and optionally crosslinked. Such polymers are described, for example, in French Patent No. FR 1 222 944 and German Patent Application No. 2 330 956, the copolymers of this type comprising an optionally N-alkylated and/or hydroxyalkylated acrylamide unit in their chain as described, for example, in Luxembourg patent application Ser. Nos. 75,370 and 75,371 or sold under the name QUADRAMER by the company American Cyanamid. Non-limiting mention may also be made of copolymers of acrylic acid and of $C_1$-$C_4$ alkyl methacrylate and terpolymers of vinylpyrrolidone, of acrylic acid and of methacrylate of $C_1$-$C_{20}$ alkyl, for example of lauryl, such as the product sold by the company ISP under the name Acrylidone® LM and methacrylic acid/ethyl acrylate/tert-butyl acrylate terpolymers such as the product sold under the name Luvimer® 100 P by the company BASF.

Non-limiting mention may also be made of methacrylic acid/acrylic acid/ethyl acrylate/methyl methacrylate copolymers as an aqueous dispersion, sold under the name Amerhold® DR 25 by the company Amerchol.

C) crotonic acid copolymers, such as those comprising vinyl acetate and/or propionate units in their chain and optionally other monomers such as allylic esters and/or methallylic esters, vinyl ether and vinyl ester of a linear and branched saturated carboxylic acid with a long hydrocarbon chain such as those comprising at least 5 carbon atoms, optionally grafted or crosslinked, or, for example, another vinyl, allylic and/or methallylic ester monomer of an α- or β-cyclic carboxylic acid. Such polymers are described, inter alia, in French Patent Nos. 1 222 944, 1 580 545, 2 265 782, 2 265 781, 1 564 110 and 2 439 798. Commercial products falling into this class are the resins 28-29-30, 26-13-14 and 28-13-10 sold by the company National Starch.

D) copolymers of $C_4$-$C_8$ monounsaturated carboxylic acids and anhydrides chosen from:

copolymers comprising (i) at least one maleic, fumaric and/or itaconic acid or anhydride and (ii) at least one monomer chosen from vinyl esters, vinyl ethers, vinyl halides, phenylvinyl derivatives, acrylic acid and its esters, the anhydride functions of these copolymers optionally bring monoesterified or monoamidated. Such polymers are described, for example, in U.S. Pat. Nos. 2,047,398, and 2,723,248 and United Kingdom Patent No. GB 839 805. Commercial products are, for example, those sold under the names Gantrez® AN or ES by the company ISP, copolymers comprising (i) at least one maleic, citraconic or itaconic anhydride unit and (ii) at least one monomer chosen from allylic and methallylic esters optionally comprising at least one acrylamide, methacrylamide, α-olefin, acrylic or methacrylic ester, acrylic or methacrylic acid or vinylpyrrolidone group in their chain, the anhydride functions of these copolymers optionally being monoesterified or monoamidated.

These polymers are described, for example, in French Patent Nos. FR 2 350 384 and FR 2 357 241.

E) polyacrylamides comprising carboxylate groups.

F) homopolymers and copolymers comprising sulfonic groups; these are polymers comprising vinylsulfonic, styrenesulfonic, naphthalenesulfonic and/or acrylamidoalkylsulfonic units.

These polymers may be chosen, for example, from:

polyvinylsulfonic acid salts having a molecular weight ranging from 1000 to 100 000, as well as the copolymers with an unsaturated comonomer such as acrylic or methacrylic acids and their esters, as well as acrylamide and its derivatives, vinyl ethers and vinylpyrrolidone;

polystyrenesulfonic acid salts such as the sodium salts that are sold for example under the names Flexan® 500 and Flexan® 130 by National Starch. These compounds are described in French Patent No. FR 2 198 719;

polyacrylamidesulfonic acid salts, such as those mentioned in U.S. Pat. No. 4,128,631 and further, for example, polyacrylamidoethylpropanesulfonic acid sold under the name Cosmedia Polymer HSP 1180 by Henkel.

Fixing anionic polyurethanes may also be used as anionic fixing polymers.

The anionic polyurethanes may be formed by an arrangement of blocks, this arrangement being obtained, for example, from:

(1) at least one compound comprising at least two active hydrogen atoms per molecule;
(2) at least one compound chosen from diols and a mixture of diols comprising acid functions and salts thereof; and
(3) at least one compound chosen from di- and polyisocyanates.

The compounds (1) may, for example, be chosen from diols, diamines, polyesterdiols and polyetherdiols, and mixtures thereof.

The compounds (1) may, for example, be chosen from linear polyethylene glycols and linear polypropylene glycols, for example, those obtained by reacting ethylene oxide and/or propylene oxide with water or diethylene glycol or dipropylene glycol in the presence of sodium hydroxide as catalyst. These polyalkylene glycols may have a molecular mass ranging from 600 to 20 000.

Other organic compounds may be chosen from those comprising mercapto, amino, carboxyl and/or hydroxyl groups. Among these, non-limiting mention may be made of polyhydroxylated compounds such as polyetherdiols, polyesterdiols, polyacetaldiols, polyamidediols, polyesterpolyamidediols, poly(alkylene ether)diols, polythioetherdiols and polycarbonatediols.

The polyetherdiols may be chosen from, for example, the products of condensation of ethylene oxide, propylene oxide and/or tetrahydrofuran, the grafted or block products of copolymerization or of condensation thereof, such as mixtures of condensates of ethylene oxide and of propylene oxide, and the products of polymerization of olefins, at high pressure, with alkylene oxide condensates. Suitable polyethers are prepared, for example, by condensation of alkylene oxides and of polyhydric alcohols, such as ethylene glycol, 1,2-propylene glycol and 1,4-butanediol.

The polyesterdiols, polyesteramides and polyamidediols may be, for example, saturated and are obtained, for example, from the reaction of saturated or unsaturated polycarboxylic acids with polyhydric alcohols, diamines and/or polyamines. Adipic acid, succinic acid, phthalic acid, terephthalic acid and maleic acid may be used, for example, to prepare these compounds. Polyhydric alcohols that are suitable for preparing polyesters may be chosen from, for example, ethylene glycol, 1,2-propylene glycol, 1,4-butanediol, neopentyl glycol and hexanediol. Amino alcohols, for example ethanolamine, may also be used. Diamines that are suitable for preparing the polyesteramides may be chosen from ethylenediamine and hexamethylenediamine.

Polyacetals may be prepared, for example, from 1,4-butanediol and/or hexanediol and formaldehyde. Suitable polythioethers may be prepared, for example, by condensation reaction between thioglycols alone or in combination with other glycols such as ethylene glycol, 1,2-propylene glycol or with other polyhydroxylated compounds. Polyhydroxylated compounds already comprising urethane groups, natural polyols, which may be further modified, for example castor oil and carbohydrates, may also be used.

For example, the compound of group (1) may be a polyesterol, for example, a polyesterdiol formed by the reaction of at least one (di)polyol ($1_a$) and at least one acid ($1_b$). The (di)polyol ($1_a$) may be chosen, for example, from neopentyl glycol, 1,4-butanediol, hexanediol, ethylene glycol, diethylene glycol, propylene glycol, butylene glycol, neopentyl glycol and (di)polyethylene glycol. The acid ($1_b$) may be chosen, for example, from phthalic acid, isophthalic acid, adipic acid and (poly)lactic acid.

A hydroxycarboxylic acid such as dimethylolpropanoic acid (DMPA) or a 2,2-hydroxymethylcarboxylic acid may, for example, be used as compound (2). In general, compound (2) may be useful as a coupling block. Compounds (2) may be chosen from those comprising at least one poly((α-hydroxycarboxylic diol) acid).

The compounds (2) may be chosen from 2,2-di(hydroxymethyl)acetic acid, 2,2-dihydroxymethylpropionic acid, 2,2-dihydroxymethylbutyric acid and 2,2-dihydroxy-methylpentanoic acid.

The compounds (3) may be chosen, for example, from hexamethylene diisocyanate, isophorone diisocyanate (IDPI), tolylene diisocyanate, 4,4'-diphenylmethane diisocyanate (DPMD) and 4,4'-dicyclohexylmethane diisocyanate (DCMD), methylenebis(p-phenyl diisocyanate), methylenebis(4-cyclohexyl isocyanate), toluene diisocyanates, 1,5-napthalene diisocyanate, 4,4'-diphenylmethane diisocyanate, 2,2'-dimethyl-4,4'-diphenylmethane diisocyanate, 1,3-phenylene diisocyanate, 1,4-phenylene diisocyanate, mixtures of 2,4- and 2,6-toluene diisocyanates, 2,2'-dichloro-4,4'-diisocyanatodiphenylmethane, 2,4-dibromo-1,5-diisocyanatonaphthalene, 1,4-butane diisocyanate, 1,6-hexane diisocyanate and 1,4-cyclohexane diisocyanate.

The anionic fixing polyurethane may be formed using an additional compound (4) that may serve to lengthen its chain. These compounds (4) may be chosen from, for example, saturated or unsaturated glycols such as ethylene glycol, diethylene glycol, neopentyl glycol and triethylene glycol; amino alcohols such as ethanolamine, propanolamine and butanolamine; heterocyclic, aromatic, cycloaliphatic and aliphatic primary amines; diamines; carboxylic acids such as aliphatic, aromatic and heterocyclic carboxylic acids, for instance oxalic acid, succinic acid, glutaric acid, adipic acid, sebacic acid and terephthalic acid; and aminocarboxylic acids. The compounds (4) may be, for example, aliphatic diols.

The anionic fixing polyurethanes may also be formed from additional compounds (5) comprising a silicone skeleton, such as polysiloxanes, polyalkylsiloxanes and polyarylsiloxanes, for example, polyethylsiloxanes, polymethylsiloxanes and polyphenylsiloxanes, optionally comprising hydrocarbon-based chains grafted onto the silicon atoms.

The fixing polyurethanes umay, for example, comprise a base repeating unit corresponding to the general formula (II):

—O—B—O—CO—NH—R$_4$—NH—CO—    (II)

wherein:
B is a divalent $C_1$ to $C_{30}$ hydrocarbon-based group, optionally substituted with a group comprising at least one carboxylic acid function and/or at least one sulfonic acid function, said carboxylic acid and/or sulfonic acid functions being in free form or partially or totally neutralized with a mineral or organic base, and
$R_4$ is a divalent group chosen from substituted and unsubstituted alkylene chosen from aromatic groups, $C_1$ to $C_{20}$ aliphatic groups and $C_1$ to $C_{20}$ cycloaliphatic groupss.

The group $R_4$ may, for example, be chosen from:

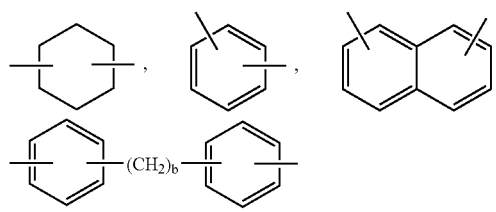

-continued

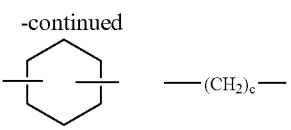

wherein:
b is a number ranging from 0 to 3; and
c is a number ranging from 1 to 20, for example, ranging from 2 to 12.

The group $R_4$ may, for example be chosen from hexamethylene, 4,4'-biphenylenemethane, 2,4-tolylene, 2,6-tolylenes 1,5-naphthylene, p-phenylene, methylene-4,4-bis(cyclohexyl) groups and the divalent group derived from isophorone.

The anionic fixing polyurethane may also comprise at least one polysiloxane block, its base repeating unit corresponding, for example, to the general formula (III):

    (III)

wherein:
P is a polysiloxane segment chosen, in at least one embodiment, from compounds of formula (IV):

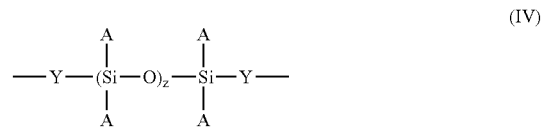    (IV)

wherein:
A, which may be identical or different, is chosen from monovalent $C_1$ to $C_{20}$ hydrocarbon-based groups that are free or substantially free of ethylenic unsaturation, and from aromatic groups,
Y is chosen from divalent hydrocarbon-based groups, and
z is a number chosen such that the weight-average molecular mass of the polysiloxane segment ranges from 300 to 10 000,
and
$R_5$ is a divalent group chosen from substituted and unsubstituted alkylene groups chosen from aromatic, $C_1$ to $C_{20}$ aliphatic and $C_1$ to $C_{20}$ cycloaliphatic groups.

The divalent group Y in formula (IV) may be chosen from the alkylene groups of formula —$(CH_2)_a$—, wherein
a is a number ranging from 1 to 10.

The groups A in formula (IV) may be chosen from alkyl groups, for example, methyl, ethyl, propyl, isopropyl, butyl, pentyl, hexyl, octyl, decyl, dodecyl and octadecyl groups; cycloalkyl groups, for example, the cyclohexyl group; aryl groups, for example, phenyl and naphthyl; arylalkyl groups, for example, benzyl and phenylethyl, and tolyl and xylyl groups.

Non-limiting examples of fixing anionic polyurethanes that may, for example, be mentioned may be chosen from the dimethylolpropionic acid/isophorone diisocyanate/neopentyl glycol/polyesterdiols copolymer (also known under the name polyurethane-1, INCI name) sold under the brand name Luviset® Pur by the company BASF, and the dimethylolpropionic acid/isophorone diisocyanate/neopentyl glycol/polyesterdiols/silicone diamine copolymer (also known under the name polyurethane-6, INCI name) sold under the brand name Luviset® Si Pur by the company BASF.

The at least one anionic fixing polymer may, in at least one embodiment, be chosen from anionic polyurethanes, acrylic acid copolymers, such as the acrylic acid/ethyl acrylate/N-tert-butylacrylamide terpolymers sold, for example, under the name Ultrahold® Strong by the company BASF, crotonic acid copolymers, such as vinyl acetate/vinyl tert-butylbenzoate/crotonic acid terpolymers and the crotonic acid/vinyl acetate/vinyl neododecanoate terpolymers sold, for example, under the name Resin 28-29-30 by the company National Starch, polymers of maleic, fumaric and/or itaconic acids or anhydrides with vinyl esters, vinyl ethers, vinyl halides or phenylvinyl derivatives, acrylic acid and its esters, such as the methyl vinyl ether/monoesterified maleic anhydride copolymers sold, for example, under the name Gantrez® by the company ISP, the copolymers of methacrylic acid and of methyl methacrylate sold under the name Eudragit® L by the company Rohm Pharma, the copolymers of methacrylic acid and of ethyl acrylate sold under the name Luvimer® MAEX or MAE by the company BASF, the vinyl acetate/crotonic acid copolymers sold under the name Luviset® CA 66 by the company BASF, and the vinyl acetate/crotonic acid copolymers grafted with polyethylene glycol sold under the name Aristoflex® A by the company BASF.

For example, the at least one anionic fixing polymer may be chosen from the silicone polyurethane sold under the name Luviset® Si Pur, the methyl vinyl ether/monoesterified maleic anhydride copolymers sold under the name Gantrez® ES 425 by the company ISP, the acrylic acid/ethyl acrylate/N-tert-butylacrylamide terpolymers sold under the name Ultrahold® Strong by the company BASF, the copolymers of methacrylic acid and of methyl methacrylate sold under the name Eudragit® L by the company Rohm Pharma, the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, the copolymers of methacrylic acid and of ethyl acrylate sold under the name Luvimer® MAEX or MAE by the company BASF, and the vinylpyrrolidone/acrylic acid/lauryl methacrylate terpolymers sold under the name Acrylidone® LM by the company ISP.

The at least one anionic fixing polymer may be present in an amount ranging from 0.05% to 25%, for example, ranging from 0.1% to 20% by weight and further, for example, ranging from 0.5% to 10% by weight, relative to the total weight of the composition.

The at least one silicone oxyalkylenated in the α and ω positions of the silicone chain as used in the presently disclosed composition may be chosen from organosilicon polymers with a linear skeleton, substituted at both ends of the main chain with oxyalkylene groups linked to the Si atoms via a hydrocarbon-based group. In at least one embodiment, the main chain does not comprise any pendent oxyalkylene groups.

In at least one embodiment, the at least one silicone oxyalkylenated in the α and ω positions of the silicone chain is chosen from compounds of formula (V):

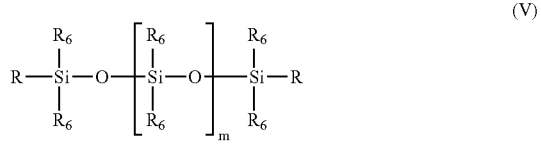

(V)

wherein:

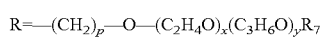

wherein:

$R_7$ is chosen from H, $CH_3$ and $CH_2CH_3$;
p is a number ranging from 1 to 5;
x is a number ranging from 1 to 100;
y is a number ranging from 0 to 50; and
each ($C_2H_4O$) and ($C_3H_6O$) unit may be distributed randomly or in blocks,
$R_6$ is independently selected from $C_1$-$C_3$ alkyls and phenyls; and
m is a number ranging from 5 to 300.

For example, the at least one silicone oxyalkylenated in the α and ω positions of the silicone chain may be chosen from compounds of formula (V) wherein:
$R_6$ is chosen from $CH_3$;
p is a number ranging from 2 to 4;
x is a number ranging from 3 to 100; and
m is a number ranging from 50 to 200.

In at least one embodiment, the average molecular weight of R ranges from 800 to 2600.

In at least one embodiment, the weight ratio of the $C_2H_4O$ units relative to the $C_3H_6O$ units ranges from 100:10 to 20:80, for example, 42:58.

In at least one embodiment, $R_7$ is a methyl group.

In at least one embodiment, the presently disclosed composition comprises the at least one silicone oxyalkylenated in the α and ω positions of the silicone chain, chosen from compounds of formula (VI):

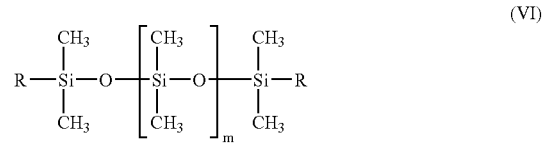

(VI)

wherein:
m is 100;
R is $(CH_2)_3$—O—$(C_2H_4O)_x(C_3H_6O)_y$—$CH_3$,
wherein:
x is a number ranging from 3 to 100; and
y is a number ranging from 1 to 50,
the weight ratio of the number of $C_2H_4O$ to the number of $C_3H_6O$ is 42:58, and
the average molecular weight of R ranges from 800 to 1500.

Among the commercial products that may contain all or some of the at least one silicone oxyalkylenated in the α and ω positions of the silicone chain, non-limiting mention may be made, for example, of those sold under the names "Abil EM 97" by the company Goldschmidt, or "KF 6009", "X22-4350", "X22-4349" or "KF 6008" by the company Shin-Etsu.

The at least one silicone oxyalkylenated in the α and ω positions of the silicone chain may be present in an amount ranging from 0.01% to 20%, for example, ranging from 0.05% to 10% by weight and further, for example, ranging from 0.1% to 5% by weight, relative to the total weight of the composition.

As propellants that may be used in the present invention, mention may be made, for example, of dimethyl ether, $C_{3-5}$ alkanes, 1,1-difluoroethane, mixtures of dimethyl ether and of $C_{3-5}$ alkanes, mixtures of 1,1-difluoroethane and of dimethyl ether and/or of $C_{3-5}$ alkanes, and in at least one embodiment, dimethyl ether alone or as a mixture.

The at least one propellant may be present in an amount ranging from 25% to 90% by weight, for example, from 35% to 80% by weight, relative to the total weight of the composition.

The cosmetically acceptable medium may, for example, be chosen from water, at least one cosmetically acceptable solvent, and mixtures thereof. For example, the cosmetically acceptable solvent may be $C_1$-$C_4$ lower alcohols, for instance ethanol, isopropanol, tert-butanol and n-butanol; polyols, for instance propylene glycol; polyol ethers; and acetone, and in at least one embodiment is ethanol.

The cosmetically acceptable medium may, for example, comprise water present in an amount less than 20% by weight, relative to the total weight of the composition.

In at least one embodiment, the composition disclosed herein may also comprise at least one common cosmetic additive chosen from silicones other than those defined above, in soluble and dispersed form, nonionic, amphoteric and cationic fixing polymers, thickeners, nacreous agents, opacifiers, UV-screening agents, sugars, fragrances, mineral, plant and/or synthetic oils, fatty acid esters, dyes, natural and synthetic mineral and organic particles, preserving agents and pH stabilizers.

A person skilled in the art will take care to select the optional additives and the amount thereof such that they do not substantially harm the properties of the compositions of the present disclosure.

These additives are, for example, present in an amount ranging from 0 to 50% by weight, relative to the total weight of the composition.

The compositions in accordance with the disclosure may be packaged in a common cosmetic aerosol device. The sprayed compositions may be in the form of a spray.

The compositions disclosed herein, sprayed from the aerosol device, may be used in rinse-out or leave-in applications, as hair fixing and/or hold compositions, haircare compositions, shampoos, hair conditioning compositions, such as compositions intended to give the hair softness, or hair makeup compositions.

According to one embodiment, the composition sprayed from the aerosol device may be used as a leave-in styling product, for example, for shaping the hair.

Another embodiment relates to a process for cosmetically treating hair comprising applying to the hair using an aerosol device a composition comprising, in a cosmetically acceptable medium, at least one anionic fixing polymer, at least one silicone oxyalkylenated in the α and ω positions of the silicone chain, and at least one propellant and leaving the composition in or rinsing it out after an optional action time. For example, the treating of the hair comprises shaping the hair. By further example, when the process comprises removing the composition from the hair, the treating comprises improving the disentangling of the hair.

Other than in the operating examples, and where otherwise indicated, all numbers expressing quantities of ingredients, reaction conditions, and so forth used in the specification and claims are to be understood as modified in all instances by the term "about." Accordingly, unless indicated to the contrary, the numerical parameters set forth in this specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The following examples are intended to illustrate the invention in a non-limiting manner.

EXAMPLE

A styling product was prepared from the following ingredients The percentages are expressed on a weight basis:

| | |
|---|---:|
| Silicone Abil EM 97 | 0.1% |
| Vinyl acetate/vinyl tert-butylbenzoate/crotonic acid copolymer | 4.9% |
| 2-Amino-2-methyl-1-propanol | 0.2% |
| Water | 16.4% |
| Ethyl alcohol | 33.4% |
| Dimethyl ether | 45% |

This composition was packaged in an aerosol device.

When sprayed onto dry hair after shaping the hairstyle, this composition allowed the shape to be held without excessive hardening and was easy to remove by brushing, leaving hair that was easy to disentangle, supple and smooth.

Similar results were obtained by replacing the propellant with 1,1-difluoroethane, and the level of fixing was adjusted by modifying the concentration of the anionic polymer and/or by adding thereto a second anionic polymer such as Luviset Si Pur from BASF.

What is claimed is:

1. A composition packaged in an aerosol device comprising, in a cosmetically acceptable medium,
   at least one anionic fixing polymer chosen from vinyl acetate/crotonic acid copolymers; vinyl acetate/crotonic acid copolymers grafted with polyethylene glycol; vinyl acetate/vinyl tert-butylbenzoate/crotonic acid terpolymers; and crotonic acid/vinyl actetate/vinyl neododecanoate terpolymers,
   at least one silicone oxyalkylenated in the α and ω positions of the silicone chain,
   chosen from compounds of formula (V):

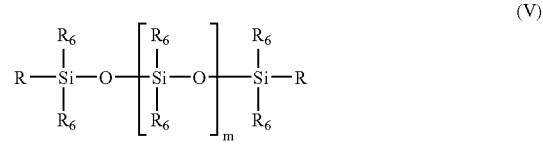

wherein:
R=—$(CH_2)_p$—O—$(C_2H_4O)_x(C_3H_6O)_y$$R_7$
wherein:
$R_7$ is chosen from H, $CH_3$ and $CH_2CH_3$;
p is a number ranging from 1 to 5;
x is a number ranging from 1 to 100;
y is a number ranging from 0 to 50; and
$R_6$ is independently chosen from a $C_1$-$C_3$ alkyl group; and
m is a number ranging from 5 to 300, and
at least one propellant present in an amount ranging from 25% to 90% by weight, relative to the total weight of the composition, and chosen from dimethyl ether, $C_{3-5}$ alkanes, 1,1-difluoroethane, mixtures of dimethyl ether and of $C_{3-5}$ alkanes, mixtures of 1,1-difluoroethane and of dimethyl ether, and mixtures of 1,1-difluoroethane and of $C_{3-5}$ alkanes, wherein the weight ratio of the $C_2H_4O$ units in R relative to the $C_3H_6O$ units in R ranges from 100:10 to 20:80, and the average molecular weight of R ranges from 800 to 2600; and wherein the composition, upon exiting the aerosol device, is in the form of a spray.

2. A composition according claim 1, wherein the at least one anionic fixing polymer is present in an amount ranging from 0.05% to 25% by weight, relative to the total weight of the composition.

3. A composition according to claim 2, wherein the at least one anionic fixing polymer is present in an amount ranging from 0.1% to 20% by weight, relative to the total weight of the composition.

4. A composition according to claim 1, wherein the at least one silicone oxyalkylenated in the α and ω positions of the silicone chain is present in an amount ranging from 0.01% to 20%, by weight, relative to the total weight of the composition.

5. A composition according to claim 4, wherein the at least one silicone oxyalkylenated in the α and ω positions of the silicone chain is present in an amount ranging from 0.05% to 10%, by weight, relative to the total weight of the composition.

6. A composition according to claim 1, wherein the at least one propellant is chosen from dimethyl ether, mixtures including at least one dimethyl ether, and 1,1-difluoroethane.

7. A composition according to claim 1, wherein the at least one propellant is present in an amount ranging from 35% to 80% by weight, relative to the total weight of the composition.

8. A composition according to claim 1, wherein the cosmetically acceptable medium is chosen from water, at least one cosmetically acceptable solvent, and mixtures thereof.

9. A composition according to claim 8, wherein the cosmetically acceptable solvent is chosen from $C_{1-4}$ lower alcohols, polyols, polyol ethers, acetones, and mixtures thereof.

10. A composition according to claim 8, wherein water is present in an amount less than 20% by weight, relative to the total weight of the composition.

11. A composition according to claim 1, wherein the composition comprises at least one cosmetic additive chosen from silicones other than those defined in claim 1, in soluble or dispersed form; nonionic, amphoteric and cationic fixing polymers; thickeners; nacreous agents; opacifiers; UV-screening agents; sugars; fragrances; mineral, plant and/or synthetic oils; fatty acid esters; dyes; natural and synthetic mineral and organic particles; preserving agents; and pH stabilizers.

12. A process for cosmetically treating hair, comprising applying to the hair with an aerosol device a composition comprising, in a cosmetically acceptable medium,
at least one anionic fixing polymer chosen from vinyl acetate/crotonic acid copolymers; vinyl acetate/crotonic acid copolymers grafted with polyethylene glycol; vinyl acetate/vinyl tert-butylbenzoate/crotonic acid terpolymers; and crotonic acid/vinyl actetate/vinyl neododecanoate terpolymers,
at least one silicone oxyalkylenated in the α and ω positions of the silicone chain, chosen from compounds of formula (V):

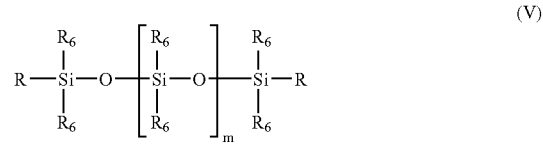

(V)

wherein:
$R=-(CH_2)_p-O-(C_2H_4O)_x(C_3H_6O)_yR_7$
wherein:
R7 is chosen from H, $OH_3$ and $CH_2CH_3$;
p is a number ranging from 1 to 5;
x is a number ranging from 1 to 100;
y is a number ranging from 0 to 50; and
$R_6$ is independently chosen from a C1-C3 alkyl group; and
m is a number ranging from 5 to 300, and
at least one propellant present in an amount ranging from 25% to 90% by weight, relative to the total weight of the composition, and chosen from dimethyl ether, $C_{3-5}$ alkanes, 1,1-difluoroethane, mixtures of dimethyl ether and of $C_{3-5}$ alkanes, mixtures of 1,1-difluoroethane and of dimethyl ether, and mixtures of 1,1-difluoroethane and of $C_{3-5}$ alkanes, and
leaving the composition in or rinsing it out after an optional action time,
wherein the weight ratio of the $C_2H_4O$ units in R relative to the $C_3H_6O$ units in R ranges from 100:10 to 20:80, and the average molecular weight of R ranges from 800 to 2600; and
wherein the composition, upon exiting the aerosol device, is in the form of a spray.

13. The process according to claim 12, wherein said composition is left in the hair.

14. A process according to claim 12, wherein the treating comprises shaping the hair.

15. A process according to claim 12, wherein said composition is removed from the hair.

16. A process according to claim 15, wherein said treating comprises improving the disentangling of the hair.

17. A composition according to claim 1, wherein:
$R_6$ is chosen from $CH_3$;
p is a number ranging from 2 to 4;
x is a number ranging from 3 to 100; and
m is a number ranging from 50 to 200.

18. A composition according to claim 1, wherein the at least one silicone oxyalkylenated in the α and ω positions of the silicone chain is chosen from compounds of formula (VI):

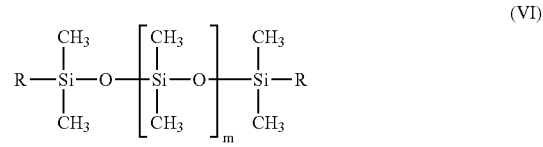

(VI)

wherein:
m is 100;
R is $(CH_2)_3-O-(C_2H_4O)x(C_3H_6O)_y-CH_3$,
wherein
x is a number ranging from 3 to 100; and
y is a number ranging from 1 to 50,
the weight ratio of the number of $C_2H_4O$ to the number of $C_3H_6O$ is 42:58, and the average molecular weight of R ranges from 800 to 1500.

* * * * *